US010765396B2

(12) United States Patent
Du et al.

(10) Patent No.: US 10,765,396 B2
(45) Date of Patent: Sep. 8, 2020

(54) X-RAY IMAGING APPARATUS AND X-RAY IMAGING SYSTEM

(71) Applicant: General Electric Company, Schenectady, NY (US)

(72) Inventors: Pengfei Du, Beijing (CN); Shaobo Gu, Beijing (CN); Jianqiang Yang, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 217 days.

(21) Appl. No.: 15/381,533

(22) Filed: Dec. 16, 2016

(65) Prior Publication Data
US 2018/0055474 A1  Mar. 1, 2018

(30) Foreign Application Priority Data
Aug. 31, 2016  (CN) .......................... 2016 1 0786258

(51) Int. Cl.
*A61B 6/00*  (2006.01)
(52) U.S. Cl.
CPC .............. *A61B 6/56* (2013.01); *A61B 6/4464* (2013.01)
(58) Field of Classification Search
CPC ........... A61B 6/4464; A61B 6/56; H05G 1/06
See application file for complete search history.

(56) References Cited

U.S. PATENT DOCUMENTS

| 5,448,608 A * | 9/1995 | Swain ..................... A61B 6/035 378/15 |
| 2006/0262906 A1 * | 11/2006 | Molz ................... A61B 6/4464 378/197 |
| 2006/0285643 A1 * | 12/2006 | Molz ..................... A61B 6/4464 378/101 |
| 2007/0165786 A1 * | 7/2007 | Grasser ................ A61B 6/4458 378/194 |
| 2008/0247516 A1 * | 10/2008 | Fink ..................... A61B 6/4464 378/194 |
| 2009/0074144 A1 * | 3/2009 | Haupl ...................... H05G 1/06 378/101 |

(Continued)

FOREIGN PATENT DOCUMENTS

GB  1205502 A  9/1970
WO  2012/111967 A2  8/2012

OTHER PUBLICATIONS

Combined Search and Examination Report issued in connection with corresponding GB Application No. 1621454.6 dated May 23, 2017.

*Primary Examiner* — David J Makiya
*Assistant Examiner* — Soorena Kefayati
(74) *Attorney, Agent, or Firm* — Fletcher Yoder, P.C.

(57) ABSTRACT

An X-ray imaging apparatus and an X-ray imaging system are described. The X-ray imaging apparatus comprises: a rail assembly, a strut assembly, an X-ray imaging assembly mounted on the strut assembly, and a power supply apparatus mounted on the strut assembly to supply power to the X-ray imaging assembly to generate X-rays for X-ray imaging. The X-ray imaging system comprises the above-mentioned X-ray imaging apparatus and a plurality of X-ray receiving apparatuses. The X-ray imaging apparatus can operate in a wide range to meet different X-ray imaging requirements, and the X-ray imaging system can complete X-ray imaging on a large number of patients in a short period of time.

8 Claims, 3 Drawing Sheets

(56) References Cited

U.S. PATENT DOCUMENTS

| | | | | |
|---|---|---|---|---|
| 2009/0154652 A1* | 6/2009 | Yi | ............................ | A61B 6/56 |
| | | | | 378/194 |
| 2010/0080360 A1* | 4/2010 | Ohta | ........................ | A61B 6/56 |
| | | | | 378/209 |
| 2011/0293070 A1* | 12/2011 | Kamiya | ................ | A61B 6/4405 |
| | | | | 378/102 |
| 2012/0207273 A1* | 8/2012 | Kim | ........................ | A61B 6/56 |
| | | | | 378/62 |
| 2012/0256099 A1* | 10/2012 | Gregerson | ............... | H05G 1/10 |
| | | | | 250/453.11 |
| 2015/0036786 A1* | 2/2015 | Katcha | ................... | A61B 6/032 |
| | | | | 378/4 |
| 2015/0036800 A1* | 2/2015 | Takemoto | ............... | A61B 6/563 |
| | | | | 378/62 |
| 2015/0117614 A1* | 4/2015 | Kim | ...................... | H02J 7/0031 |
| | | | | 378/102 |
| 2015/0267428 A1* | 9/2015 | Wall | .......................... | E04H 3/08 |
| | | | | 52/173.1 |
| 2015/0305699 A1* | 10/2015 | Sakuragi | ............. | A61B 6/4405 |
| | | | | 250/493.1 |
| 2016/0029984 A1* | 2/2016 | Jang | ....................... | A61B 6/547 |
| | | | | 378/189 |
| 2017/0025890 A1* | 1/2017 | Splinter | ................ | H02J 7/1415 |
| 2017/0128030 A1* | 5/2017 | Kong | ................... | A61B 6/4464 |

\* cited by examiner

X-RAY IMAGING APPARATUS AND X-RAY IMAGING SYSTEM

FIELD

The exemplary non-limiting embodiments presented herein relate to an X-ray imaging apparatus and an X-ray imaging system.

BACKGROUND

A suspended-on-ceiling X-ray imaging apparatus provides an X-ray imaging assembly on a rail mounted on a ceiling via a suspension apparatus, and enables the X-ray imaging assembly to move back and forth along the rail to meet requirements for X-ray imaging at different positions. In the existing suspended X-ray imaging apparatus, it is needed to use a high voltage cable to connect the X-ray imaging assembly with a high voltage generation unit, and provide enough power to the X-ray imaging assembly to generate X-rays. In addition to having the high voltage cable follow the X-ray imaging assembly to move, it is also needed to have the high voltage cable fixed and housed in the air or hung in a ring-shape below the ceiling by a cable management apparatus.

FIG. 1 is a schematic view of a prior suspended X-ray imaging apparatus. As shown in FIG. 1, the suspended X-ray imaging apparatus comprises: a rail assembly 201 to be mounted on a ceiling; a telescopable strut assembly 202 mounted onto the rail assembly 201 and which may move linearly along the rail assembly 201; a high voltage generation unit 203; a high voltage cable 204 for connecting the high voltage generation unit 203 with the strut assembly 202; and a high-voltage cable guide mechanism 205, wherein the strut assembly 202 further comprises an X-ray tube 206 mounted thereon and moving along with it. The high voltage generation unit 203 provides the X-ray tube 206 with power via the high voltage cable 204 for the X-ray tube 206 to generate X-rays. The high-voltage cable guide mechanism 205 comprises a plurality of guide hooks provided along and able to move along the rail assembly 201, and the high voltage cable 204 is guided by the plurality of guide hooks along the rail assembly 201. The high voltage cable 204 has slack portions away from the guide hooks, hanging in a way similar to a curtain in the lower space of the rail assembly 201 which does not affect the movement and operation of the strut assembly, and the slack portions may move along with the linear movement of the strut assembly 202.

Since the high voltage generation unit is usually mounted or placed on a floor of a room where the X-ray imaging apparatus locates, the operation range of the X-ray imaging apparatus is restricted by the length of the high voltage cable which is connected between the X-ray imaging unit and the high voltage generation unit. A longer high voltage cable not only allows the X-ray imaging apparatus to have a wider range of movement and a better functionality, but also provides more convenience for a user. However, a drawback of the longer high voltage cable is the increased difficulty of cable management, which affects the normal operation of the X-ray imaging apparatus. Therefore, in the prior art, the length of a high voltage cable in a suspended X-ray imaging apparatus is usually limited to 20 meters to 40 meters, where the X-ray imaging apparatus is not able to move in a wide range to meet different X-ray imaging requirements.

In addition, a suspended X-ray imaging apparatus in the prior art is usually provided in a radiation room to perform X-ray imaging shooting to a patient on a single operation/detection bed. However, in some situations, for example, in an emergency room, it is inconvenient to transfer a large number of patients into the radiation room to perform individual shootings in turn. Thus, it is required to provide an X-ray imaging system which is able to complete X-ray imaging to patients on a plurality of detection beds in a shorter period of time.

SUMMARY

In at least one aspect, the exemplary non-limiting embodiments presented herein provide an X-ray imaging apparatus which can operate in a wide range to meet different X-ray imaging requirements and enable X-ray imaging on a large number of patients in a short period of time.

An exemplary non-limiting embodiment provides an X-ray imaging apparatus, comprising: a rail assembly; a strut assembly mounted to the rail assembly and configured to be telescopable in a vertical direction and be able to move linearly along the rail assembly; and an X-ray imaging assembly mounted on the strut assembly;

the X-ray imaging assembly further comprises a chargeable and dischargeable power supply apparatus mounted on the strut assembly, the power supply apparatus being used for supplying power to the X-ray imaging assembly to generate X-rays.

Optionally, a charging apparatus for charging the power supply apparatus is provided on the rail assembly.

Optionally, a connector for connecting the power supply apparatus with the charging apparatus is provided on the strut assembly.

Optionally, the charging apparatus comprises at least one charging station provided at a predetermined position of the rail assembly, the at least one charging station being configured to be electrically connected to the power supply apparatus and charge the power supply apparatus, when the strut assembly moves to the predetermined position along the rail assembly.

Optionally, the charging apparatus comprises a slip ring provided along the rail assembly, the slip ring being configured to be electrically connected to the power supply apparatus, and charge the power supply apparatus when the strut assembly moves to any position along the rail assembly.

Optionally, the X-ray imaging assembly comprises an X-ray tube for generating X-rays, the X-ray tube being connected to the power supply apparatus.

Optionally, the X-ray imaging apparatus further comprises a power converter provided on the X-ray imaging assembly, the power converter being connected to the power supply apparatus and configured to convert power generated by the power supply apparatus to power required for generating X-rays by the X-ray tube.

Optionally, the X-ray imaging apparatus further comprises a control unit for controlling the X-ray imaging assembly to generate X-rays, the power supply apparatus being further used for supplying power to the control unit.

An exemplary non-limiting embodiment further provides an X-ray imaging system comprising: the X-ray imaging apparatus included in any one of the above described. and an X-ray receiving apparatus configured to receive the X-rays generated by the X-ray imaging apparatus and passing through a target object to be imaged, and to convert the received X-rays into electrical signals.

Optionally, the X-ray receiving apparatus comprises a plurality of X-ray receiving apparatuses located at a plurality of positions, the X-ray imaging apparatus being configured to be able to move along the rail assembly to positions corresponding to the plurality of X-ray receiving apparatuses, to cooperate with a corresponding X-ray receiving apparatus to perform X-ray imaging.

It may be seen from the summary of the technical solutions described above that, providing the chargeable and dischargeable power supply apparatus onto the X-ray imaging apparatus not only makes the X-ray imaging apparatus be free from the restriction on the operation range of the X-ray imaging apparatus due to the high voltage cable length, expanding its movement and operation range; but also enables the X-ray imaging system including the X-ray imaging apparatus to operate flexibly in various situations, for example, in an emergency room, to rapidly examine a large number of patients and complete X-ray imaging.

Other features and aspects will be apparent through the following detailed description, figures and claims.

BRIEF DESCRIPTION OF THE DRAWINGS

The exemplary non-limiting embodiments presented herein can be better understood in light of the description of said embodiments with reference to the accompanying drawings, in which.

DETAILED DESCRIPTION

Hereafter, a detailed description will be given for preferred embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for one of ordinary skilled in the art associated with the contents disclosed in the present disclosure, which should not be regarded as insufficient disclosure of the present disclosure.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present application do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

Figure 1:
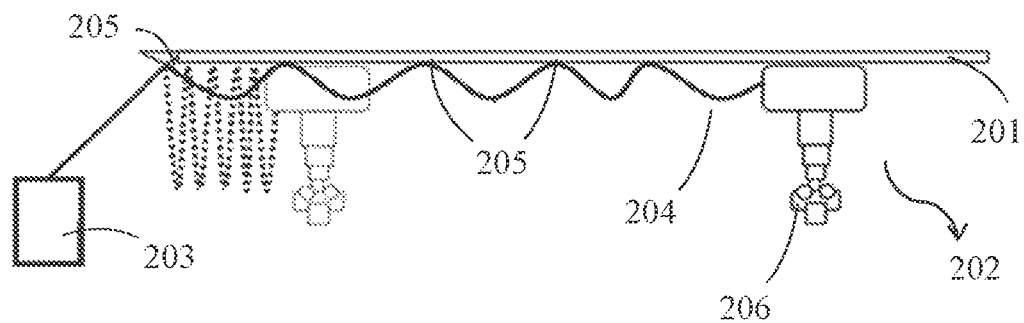
FIG. 1 is a schematic view of a prior art suspended X-ray imaging apparatus.
Figure 2:
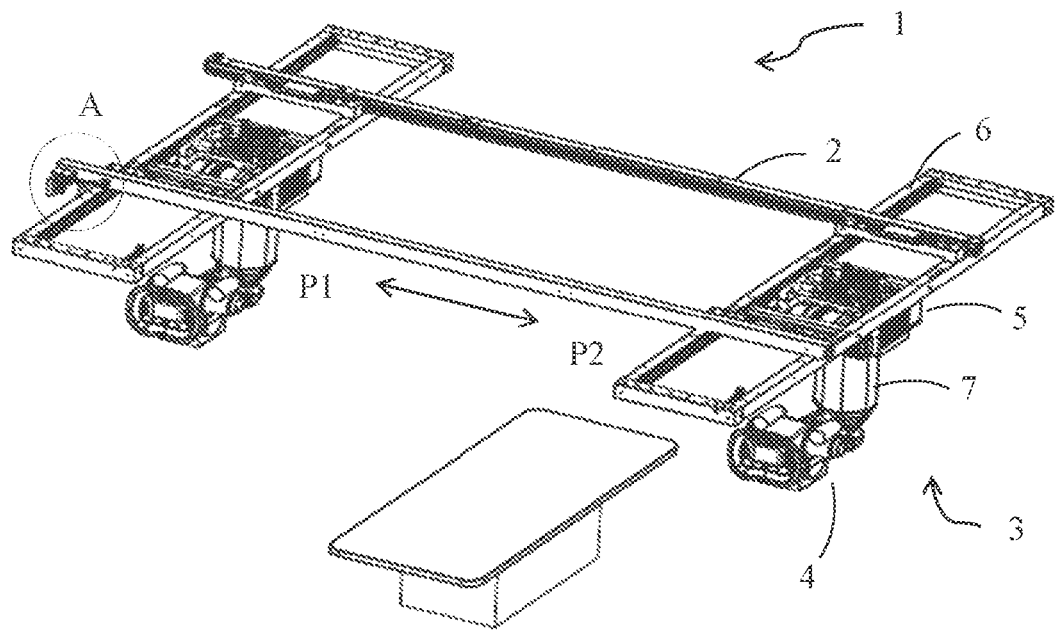
FIG. 2 is a schematic view of an exemplary non-limiting embodiment of an X-ray imaging apparatus.

FIG. 2 is a schematic view of an X-ray imaging apparatus according to an exemplary non-limiting embodiment of the present invention. As shown in FIG. 2, a X-ray imaging apparatus 1 comprises: a rail assembly 2, a strut assembly 3 mounted on the rail assembly 2, an X-ray imaging assembly 4 mounted on the strut assembly 3 and a chargeable and dischargeable power supply apparatus 5 mounted on the strut assembly 3. The strut assembly 3 is telescopable in a vertical direction and is able to move linearly along the rail assembly 2. The power supply apparatus 5 is used for supplying power to the X-ray imaging assembly to generate X-rays.

In an exemplary non-limiting embodiment, the rail assembly 2 is mounted on a ceiling or the like surface, constituting a longitudinal positioning rail, wherein, the rail assembly 2 may consist of one track or a plurality of tracks.

The strut assembly 3 comprises a carriage 6, and is mounted on the rail assembly 2 via the carriage 6. By the guidance of the carriage 6, the strut assembly 3 may move longitudinally along the rail assembly 2, for example, as indicated by the arrows in FIG. 2, moving from Position P1 to Position P2, or from Position P2 to Position P1.

Figure 3:
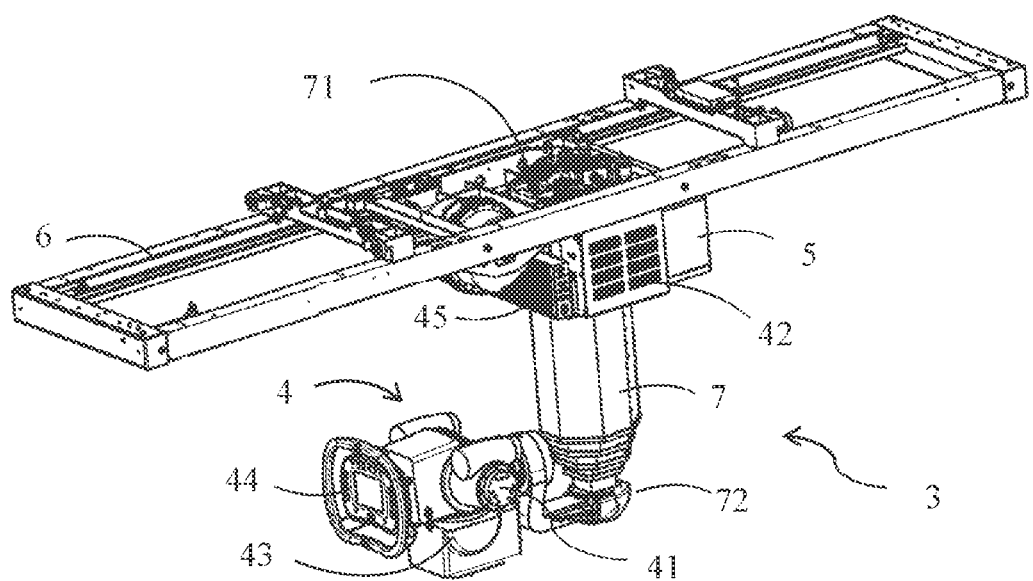
FIG. 3 is a schematic view of an exemplary non-limiting embodiment of a strut assembly of the X-ray imaging apparatus in FIG. 2.
Figure 4:
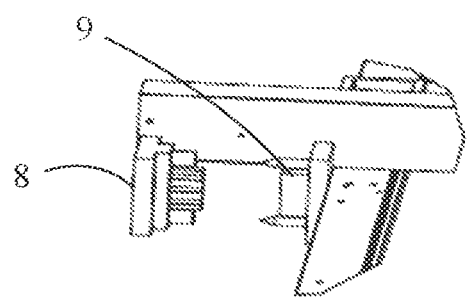
FIG. 4 is an enlarged view of Part A of the X-ray imaging apparatus in FIG. 2.

FIG. 3 is a schematic view of an exemplary embodiment of a strut assembly of the X-ray imaging apparatus in FIG. 2; FIG. 4 is an enlarged view of Part A of the X-ray imaging apparatus in FIG. 2. To perform X-ray imaging to a target to be detected, it is necessary to position the X-ray imaging assembly 4 near the target to be detected. Referring to FIG. 3, the strut assembly 3 of an exemplary non-limiting embodiment may further comprise an extendable column 7. The extendable column 7 comprises a carriage mounting end 71 and a to-be-detected target orientation end 72. The carriage 6 is mounted to the carriage mounting end 71, and the X-ray imaging assembly 4 is mounted to the to-be-detected target orientation end 72. The to-be-detected target orientation end 72 may move towards the carriage mounting end 71 and away from the carriage mounting end 71, to telescope the extendable column 7, so that the to-be-detected target orientation end 72 and the X-ray imaging assembly 4 mounted thereon may be positioned to approach the target to be detected.

The power supply apparatus 5 may provide a voltage for generating X-rays to the X-ray imaging assembly 4, and when the power supply apparatus 5 is connected with an external power supply (not shown in the figure), the power supply apparatus 5 may be charged by the external power supply. According to an exemplary non-limiting embodiment, the power supply apparatus 5 may move on the rail assembly 2 along with the strut assembly 3 and the X-ray imaging assembly 4, and may provide a voltage directly to the X-ray imaging assembly 4 at any position within a movement range to generate X-rays to complete X-ray imaging. This makes the X-ray imaging apparatus be free from the restriction on its movement and operation range due to a high voltage cable.

As shown in FIG. 2 and FIG. 4, a charging apparatus 8 is provided on the rail assembly 2, and is connected to the external power supply, The power supply apparatus 5 may obtain power supply from the external power supply via the charging apparatus 8. A connector 9 is provided on the strut assembly 3. When the strut assembly 3 moves along the rail assembly 2 to a position where the charging apparatus 8 is provided, the power supply apparatus 5 will be electrically connected to the charging apparatus 8 via the connector 9.

According to an exemplary non-limiting embodiment, the charging apparatus 8 comprises one or more charging stations provided on the rail assembly 2, wherein each of the charging stations is provided at a predetermined position of the rail assembly 2. The charging station may be configured to be electrically connected to the power supply apparatus 5 and charge the power supply apparatus 5 when the power supply apparatus 5 moves along the rail assembly 2 with the strut assembly 3 to the predetermined position where the charging station locates; and to end the charging process when the electrical connection is lost between the power supply apparatus 5 and the charging station. The power supply apparatus 5 may supply power to the X-ray imaging assembly 4 at any time according to a user operation instruction to perform X-ray imaging.

According to another exemplary non-limiting embodiment, the charging apparatus 8 comprises a slip ring (not shown in figures) provided on the rail assembly 2, wherein the slip ring may be provided along the whole rail assembly 2. The slip ring may be configured to be electrically connected to the power supply apparatus 5 and charge the power supply apparatus 5 when the strut assembly 3 moves to any position along the rail assembly 2.

In addition, the slip ring may also be provided at a predetermined position along a portion of the rail assembly. In this situation, the charging station may be configured to be electrically connected to the slip ring and charge the power supply apparatus 5 when the power supply apparatus 5 moves along the rail assembly 2 with the strut assembly 3 to the predetermined position; and to end the charging process when the electrical connection is lost between the power supply apparatus 5 and the slip ring.

As shown in FIG. 3, the X-ray imaging assembly 4 comprises an X-ray tube 41, a power converter 42, a collimator 43, and a user control interface 44, wherein, the X-ray tube 41 is connected to the power supply apparatus 5 for generating X-rays. The power converter 42 is connected to the power supply apparatus 5, and converts the power generated by the power supply apparatus 5 to the power required for generating X-rays by the X-ray tube.

In addition, a control unit 45 is further provided on the X-ray imaging apparatus 4. The control unit 45 may be used for controlling the X-ray imaging apparatus 4 to perform X-ray imaging, for example, the control unit 45 may control the X-ray tube 41 to generate X-rays, or control the operation of the collimator 43 to control the radiation field of the X-rays. The power supply apparatus 5 may be further used for supplying power to the control unit 45.

Figure 5:
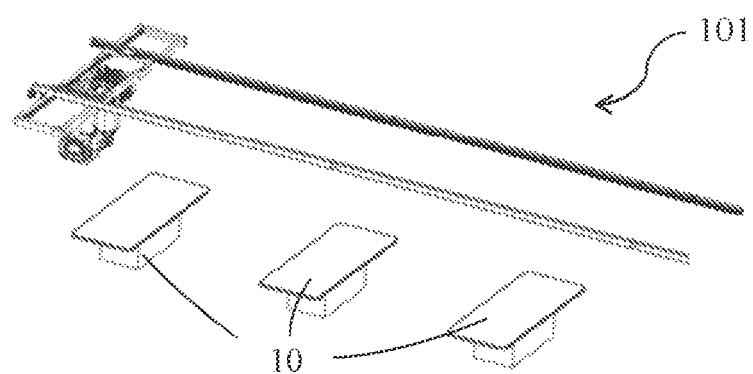
FIG. 5 is a schematic view of an exemplary non-limiting embodiment of an X-ray imaging system.

FIG. 5 is a schematic view of an exemplary non-limiting embodiment of an X-ray imaging system. As shown in FIG. 5, an X-ray imaging system 101 comprises: the X-ray imaging apparatus 1 described above and an X-ray receiving apparatus 10. The X-ray receiving apparatus 10 is used to receive the X-rays generated by the X-ray imaging apparatus 1 and passing through the target object to be imaged, and to convert the received X-rays into electrical signals.

According to an exemplary non-limiting embodiment, the X-ray receiving apparatus 10 comprises a plurality of X-ray receiving apparatuses located at a plurality of positions. The X-ray imaging apparatus 1 is able to move along the rail assembly 2 to positions corresponding to the plurality of X-ray receiving apparatuses 10, so as to cooperate with a corresponding X-ray receiving apparatuses 10 to perform X-ray imaging.

Since the X-ray imaging apparatus 1 provides on the strut assembly 3 the power supply apparatus 5 which may supply power to the X-ray imaging assembly to generate X-rays, the X-ray imaging apparatus 1 is free from the restriction due to the high voltage cable which connects the external power supply with the X-ray imaging assembly 4 in the prior art. Therefore, the X-ray imaging apparatus 1 has the advantages of being more flexible in use and having a wider operation range. In addition, the provision of the charging apparatus 8 connected with the external power supply on the rail assembly 2 enables the X-ray imaging apparatus 1 to charge the power supply 5 when it is idle, which assures the endurance time of the X-ray imaging apparatus 1.

Since the X-ray imaging system comprises the X-ray imaging apparatus 1 described above and the plurality of X-ray receiving apparatuses 10 located at the plurality of positions, the X-ray imaging system 101 can complete X-ray imaging on a plurality of targets to be detected at different positions in a short period of time, which is adapted to operate flexibly in various situations, for example, in an emergency room, to rapidly examine a large number of patients and complete X-ray imaging.

Some exemplary embodiments have been described in the above. However, it should be understood that various modifications may be made thereto. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other implementation also falls within a protection range of the Claims.

What is claimed is:

1. An X-ray imaging apparatus comprising:
   a rail assembly;
   a strut assembly mounted to the rail assembly and configured to be extendable and movable along the rail assembly;
   an X-ray imaging assembly mounted on the strut assembly, wherein the X-ray imaging assembly comprises an X-ray tube for generating X-rays;
   a power supply apparatus mounted on the strut assembly to supply power to the X-ray imaging assembly to generate X-rays via the X-ray tube, the power supply apparatus being rechargeable, wherein the power supply apparatus is configured to move with the strut assembly along the rail assembly and to supply power to the X-ray assembly to enable the X-ray tube to generate X-rays at any position along the rail assembly; and
   a charging apparatus provided on the rail assembly to charge the power supply apparatus, the charging apparatus comprising at least one charging station provided at a predetermined position on the rail assembly and electrically connected to the power supply apparatus to charge the power supply apparatus when the strut assembly moves to the predetermined position along the rail assembly, wherein the charging apparatus is configured to stop charging the power supply apparatus when the strut assembly moves away from the predetermined position.

2. The X-ray imaging apparatus of claim 1, further comprising a connector provided on the strut assembly to connect the power supply apparatus to the charging apparatus.

3. The X-ray imaging apparatus of Claim 1, further comprising a power converter provided on the X-ray imaging assembly, the power converter connected to the power supply apparatus and configured to convert power generated by the power supply apparatus to power required for generating X-rays by the X-ray tube.

4. The X-ray imaging apparatus of claim 1, wherein the strut assembly is configured to be telescoping in a vertical direction and movable linearly along the rail assembly.

5. An X-ray imaging system comprising:
   the X-ray imaging apparatus according to claim 1; and
   an X-ray receiving apparatus configured to receive the X-rays generated by the X-ray imaging apparatus that pass through a target object to be imaged and convert the received X-rays into electrical signals.

6. The X-ray imaging apparatus of claim 3, further comprising a control unit for controlling the X-ray imaging assembly to generate X-rays, and the power supply apparatus supplies power to the control unit.

7. The X-ray imaging system of claim 5, wherein the X-ray receiving apparatus comprises a plurality of X-ray receiving apparatuses located at a plurality of positions, and the X-ray imaging apparatus is configured to move along the rail assembly to positions corresponding to the X-ray receiving apparatuses to cooperate with a corresponding X-ray receiving apparatus to perform X-ray imaging.

8. The X-ray imaging apparatus of Claim 5, wherein the strut assembly is configured to be telescoping in a vertical direction and movable linearly along the rail assembly.

* * * * *